United States Patent [19]

Zimmel et al.

[11] Patent Number: 5,035,691
[45] Date of Patent: Jul. 30, 1991

[54] HOT-MELT MOISTURE INDICATOR MATERIAL FOR DISPOSABLE ARTICLES

[75] Inventors: John M. Zimmel, St. Paul; Mark G. Katsaros, Mahtomedi; William L. Bunnelle, Hugo, all of Minn.

[73] Assignee: H. B. Fuller Licensing & Financing Inc., Wilmington, Del.

[21] Appl. No.: 546,022

[22] Filed: Jun. 28, 1990

[51] Int. Cl.$^5$ .................. A61F 13/15; A61F 13/20; C08L 15/00
[52] U.S. Cl. .................................. 604/361; 523/111
[58] Field of Search ...................... 604/361; 523/111

[56] References Cited

U.S. PATENT DOCUMENTS

| | | | |
|---|---|---|---|
| 3,731,685 | 5/1973 | Eidus | 128/284 |
| 3,759,261 | 9/1973 | Wang | 128/287 |
| 3,860,003 | 1/1975 | Buell | 128/287 |
| 3,918,433 | 11/1975 | Fuisz | 128/2 F |
| 3,918,454 | 11/1975 | Korodi et al. | 128/287 |
| 3,952,746 | 4/1976 | Summers | 128/287 |
| 4,050,462 | 9/1977 | Woon et al. | 128/287 |
| 4,192,311 | 3/1980 | Felfoldi | 128/287 |
| 4,231,370 | 11/1980 | Mroz et al. | 128/287 |
| 4,253,461 | 3/1981 | Strickland et al. | 128/287 |
| 4,326,528 | 4/1982 | Ryan et al. | 128/287 |
| 4,383,057 | 5/1983 | Yamamoto et al. | 523/333 |
| 4,400,229 | 8/1983 | Demmer et al. | 156/307.5 |
| 4,681,576 | 7/1987 | Colon et al. | 604/361 |
| 4,743,238 | 5/1988 | Colon et al. | 604/361 |
| 4,895,567 | 1/1990 | Colon et al. | 604/361 |

FOREIGN PATENT DOCUMENTS 678754   1/1964  Canada .
2031104 12/1971  Fed. Rep. of Germany .

Primary Examiner—David J. Isabella
Assistant Examiner—Elizabeth M. Burke
Attorney, Agent, or Firm—Merchant, Gould, Smith, Edell, Welter & Schmidt

[57] ABSTRACT

Polyester-based hot-melt moisture indicator material for disposable articles containing a polyester, a carboxylic acid and an acid-base indicator.

7 Claims, No Drawings

HOT-MELT MOISTURE INDICATOR MATERIAL FOR DISPOSABLE ARTICLES

FIELD OF THE INVENTION

The invention relates to hot-melt materials that can be used in disposable articles to indicate when moisture is introduced into the disposable article during use. The hot-melt materials are typically placed in fluid communication with the absorbent material held within the disposable article. As the hot-melt moisture indicator material comes into contact with a source of moisture, the material changes color. Such a moisture indicator material can provide assistance to individuals caring for infants, incontinent persons, or other patients in a supportive or medical environment for the purpose of enabling the caretaker to change or replace the disposable article in a timely manner with minimal discomfort to the patient wearing the article.

BACKGROUND OF THE INVENTION

Disposable articles and their manufacture from construction materials, including absorbent materials, woven and nonwoven fabrics, films, and adhesives, are described in a variety of U.S. Pat. Nos. including Buell, U.S. Pat. No. 3,860.003; Woon et al., U.S. Pat. No. 4,050,462; Strickland et al., U.S. Pat. No. 4,253,461; and Ryan et al., U.S. Pat. No. 4,326,528.

Disposable articles, such as diapers, are typically manufactured by combining a fluid-impervious film-backing sheet, absorbent materials and a fibrous, fluid-permeable hydrophobic top-sheet. Such diapers typically also have an elastic band attached to the portion of the diaper forming a leg opening. Such diapers additionally contain tabs for securing the article on the individual. The film-backing sheet provides a barrier preventing leakage of the article.

Such disposable articles are made in continuous processing by passing the materials of construction through high speed machines. In such continuous processing, components of the disposable article are continuously adhered to one another, and the disposable article is cut after assembly. Typically, the components are added to a polymer film in stages, including an addition of an elastic, an addition of a disposable, absorbent layer, and an optional addition of waist shields, attachment tabs, and other components. Any material added to the disposable article must have, as an essential property, ease of application at high construction application speeds.

Typical of such disposable articles are disposable infant diapers and disposable incontinent pads for adult patients. During the use of such disposable diapers and incontinent pads, disposable articles become wet and require replacement to ensure adequate humane care of the infant and adult patients. In the past, the wetness of the articles were monitored manually by either the visual or tactile inspection of the internal absorbent materials held within the impervious film-backing sheet. Such an inspection can be time consuming and often can be unpleasant.

In view of the nature of visual or tactile inspections of the disposable articles, development of moisture indicators that either change from colorless to colored or change from one color to another color in the presence of moisture were developed. Mroz et al., U.S. Pat. No. 4,231,370, discloses an aqueous latex or dispersion including a polymer adhesive-like material and an indicator in an aqueous base. A line of the Mroz materials are apparently spray-applied to the inside of the flexible film-backing sheet of the disposable articles. The indicator adheres to the polyethylene and dries to a flexible coating that is light yellow in color. The indicator, when wet during use, changes from a light yellow to a blue appearance.

The Colon et al. patents, U.S. Pat. Nos. 4,681,576, 4,743,238, and 4,895,567, teach wetness-indicating hot-melt adhesives which change in response to the presence of moisture based on a polyvinyl pyrrolidone, a polyvinyl pyrrolidone-vinyl acetate polymer, or an ethylene-acrylic acid polymer in combination with an organic acid and a wetness-indicating agent. The patents teach that the compositions can contain a variety of other ingredients, such as water-soluble waxes, glycerol esters, hydrogenated oils, and a variety of polymeric materials such ethylene-vinyl acetate copolymers, etc.

We have found that the aqueous latexes, such as those disclosed in Mroz et al., require increased manufacturing time to permit the evaporation of the aqueous portion of the latex. Such a requirement reduces the speed at which the disposable articles can be manufactured. We have also found that in typical formulations of hot-melt indicator material during manufacture the molten indicator can be phase unstable. Such phase instability can cause the indicator to be nonfunctional after application. While such phase instability can be remedied by introducing agitation into the hot-melt applicator machines, a need exists to formulate hot-melt indicator materials that are phase stable during manufacture and application.

BRIEF STATEMENT OF THE INVENTION

We have found an improved hot-melt moisture indicator composition that can be used in the construction of disposable articles using hot-melt technology. The hot-melt moisture indicator material is easily applied to disposable article construction materials, rapidly indicates the presence of moisture during use, and is physically and chemically stable under conditions of manufacture, application and use. The hot-melt moisture indicator compositions of the invention, which display significantly improved properties over the materials of the prior art, comprise a polyester material manufactured by esterifying an ethylenically unsaturated polymer, having pendant carboxyl groups, with a hydrophilic hydroxy group-containing compound to form a stable, hot-melt polyester-based material which is combined with a $C_{5-35}$ carboxylic acid material, and an acid-base indicator displaying a color change at a pH of about 2 to 5.6, preferably about 3.8 to 5.4.

DETAILED DESCRIPTION OF THE INVENTION

We have found that a phase-stable, hot-melt polyester material can be used as a moisture indicator in disposable articles. In use, the material is extruded onto the components of the disposable article, typically the film-backing layer, in a thin line. The composition is positioned to come into contact with moisture as soon as the moisture is introduced into the absorbent portion of the disposable article. The hot-melt indicator material typically comprises about 50 to 90 wt-% of a polyester material which is a reaction product between a vinyl polymer, which can be carboxylated or can have units derived from an ethylenically unsaturated monomer with a pendant carboxylic acid group, and a hydrophilic hydroxy compound. The polyester is used in combination with a carboxylic acid composition, having about 5 to 35 carbon atoms, and an effective amount of an acid-base indicator material having a color change at pH of about 2 to 5.6. The carboxylic acid compound is typically present in the hot-melt moisture indicator composition in a range of about 10 to 50 wt-% of the total composition. The indicator material may also preferably have other common hot-melt ingredients that enhance or stabilize hot-melt or indicator properties.

THE POLYESTER REACTION PRODUCT

The polyester reaction product forming the hot-melt base composition of the invention is preferably a thermoplastic polyester. It is preferably formed by reacting a vinyl polymer having pendant carboxylic acid groups and a hydrophilic hydroxy compound. The polyester material is typically made under common esterification reaction conditions to promote reaction of the hydroxy compound with the acid groups pendant upon the polymer material.

The vinyl polymer material is a polymer made from ethylenically unsaturated monomers and has a polymer molecular weight of about 1000 to 5000. The vinyl polymer contains pendant carboxyl groups that are preferably derived from an ethylenically unsaturated monomer having pendant carboxylic acid groups. Examples of useful monomer materials with a pendant carboxylic acid group include acrylic acid, methacrylic acid, maleic anhydride, maleic acid, fumaric acid, itaconic acid, vinyl benzoic acid such as 4-vinyl benzoic acid, or other vinyl monomers wherein an ethylenically unsaturated group is linked to a carboxylic acid group through typically a substantially hydrocarbon, alkylene, or arylene moiety.

The vinyl polymer can also contain noncarboxylic acid-containing monomers such as ethylene, propylene, butylene, and the like. This group of noncarboxylic acid-containing monomers also includes vinyl acetate, methyl acrylate, methyl methacrylate, ethyl acrylate, isobutyl methacrylate, di-esters of maleic or fumaric acids, styrene, vinyl toluene, and the like.

Exemplary polymer compositions are ethylene-acrylic acid copolymers; ethylene-methacrylic acid copolymers; ethylene-ethyl acrylate-methacrylic acid terpolymers; acrylic acid terpolymers; acrylic acid-methyl methacrylate copolymers; ethylene-vinyl acetate-methacrylic acid terpolymers; ethylene-vinyl acetate-acrylic acid terpolymers; ethylene-methyl acrylate-methacrylic acid terpolymers; ethylene-vinyl acetate-monoethyl maleate terpolymers; ethylene-methyl methacrylate-maleic acid terpolymers; ethylene-vinyl benzoic acid copolymers; ethylene-vinyl acetate-vinyl benzoic acid terpolymers; styrene-maleic acid copolymers; styrene-acrylic acid copolymers; ethylene-stryene-acrylic acid copolymers; and others.

The above vinyl polymers containing pendant carboxylic acid groups are typically produced by direct polymerization of the ethylenically unsaturated carboxylic acid-containing monomer material. Alternatively, a vinyl polymer can be carboxylated after polymerization of noncarboxylic acid-containing monomers by reacting the resultant polymer with a carboxylic acid group-containing monomer or with other carboxylating agents using known techniques to form known polymers with free carboxylic acid groups.

Such polymers have a molecular weight of about 1000 to 5000 and a melt viscosity at 140° C. of about 200 cP to 2000 cP. Preferably such polymers have an acid number within the range of about 117 to 234, more preferably within the range of about 148 to 203. Such characteristics are important in obtaining a stable hot-melt material having sufficient polyester functionality in the final product to obtain phase and chemical stability during manufacture, application, and use.

PREFERRED

The preferred vinyl polymer material for use in the invention comprises a copolymer containing a $C_{2-4}$ alphaolefin and a sufficient amount of an ethylenically unsaturated monomer material having pendant carboxylic groups such that the acid number of the vinyl polymer is within the range of about 148 to 203. Preferably this monomer material is either acrylic acid or methacrylic acid. The alpha-olefin useful in manufacturing these polymers comprises ethylene, propylene, 1-butene, 2-butene, etc. More preferably, the vinyl polymer is an ethylene copolymer containing about 70 to 85 wt-%, most preferably about 74 to 81 wt-%, of ethylene. The most preferred vinyl polymer for use in manufacturing the polyester material of the invention is an ethylene-acrylic acid copolymer having 19 to 26 weight percent acrylic acid, and a melt viscosity of 500 cP to 1000 cP at 140° C. Such a material is sold under the trade name of AC 5180, manufactured by Allied Corp.

The carboxylic acid-containing vinyl polymer described above is reacted with a hydroxy functional hydrophilic compound under esterification conditions to produce the polyester-based compound of the invention. Such hydrophilic hydroxy-containing compounds typically have a molecular weight of about 1,000 to 15,000, preferably about 5,000 to 10,000; typically have one or more hydroxy groups; and are at least mildly hydrophilic. Preferably, the hydroxy-functionalized compound is of the formula $H(OCH_2CH_2)_nOH$ or $CH_3(OCH_2CH_2)_nOH$ wherein n is about 45 to 300.

A hydroxy-substituted hydrophilic compound of the invention provides a number of functions to the compositions, including enhancing the formation of uniform homogeneous phase-stable compositions. Further, the hydroxy-substituted compound tends to produce adhesives with workable viscosity and a controlled hydrophilicity. Lastly, the judicious manufacture of the material from the hydroxy-group compounds can reduce the pressure-sensitive properties of the material of the invention. The important aspects of the hydroxy-substitute organic compound is that it contains one or more hydroxy groups attached to an essentially organic composition resulting in at least some hydrophilic character. Preferred hydroxy-substituted organic compounds include polyalkylene oxide polymers having a molecular weight greater than 1,000 made from polyethylene oxide, polypropylene oxide, or mixtures thereof (such as CARBOWAX®). The most preferred hydroxy compound for use in the invention comprises a polyethylene oxide polymer having a molecular weight of at least 2,000. Such materials are sold as CARBOWAX®, having molecular weights averaging about 2,000, 4,000, 8,000, etc.

The polyester material is manufactured by reacting the acid-functional copolymer and the hydroxy-functional material at typical esterification conditions. Generally, the reactants are solid materials at room temperature, and must initially be melted and blended at elevated temperatures. The reactants, after being heated, melted, and blended, can be stabilized using antioxidant materials, such as a phenol antioxidant. Typically, the reactions are conducted in large mixing vessels under a nitrogen atmosphere with agitation. The esterification reaction is typically promoted using commonly known esterification catalysts, including metal oxides, organic sulfonic acids, mineral acids, and others. A preferred catalyst is monobutyl tin (IV) oxide. Water of reaction is generated during the esterification reaction which is typically removed under vacuum. After the reaction has proceeded to the desired extent and the material is cooled, additional quantities of antioxidant can be added to preserve the material during storage, disposable-article manufacture, and use.

We have found that, depending on the amounts of material, the manufacture of the polyester can result in the conversion of the majority of both the acid functional polymer and the hydroxy-functional compound in the polyester material. When the polymer carboxylic acid functionality is in excess, depending on reaction conditions, less than 10 percent of the hydroxy-functional material is typically unreacted at the end of the procedure while each polymer molecule is at least partially esterified to the extent that hydroxy compound is available for reaction.

CARBOXYLIC ACID MATERIALS

Carboxylic acids, e.g., fatty acids, are useful in the moisture-indicator materials of the invention. The polyester material described above and the fatty acid material cooperate to form a continuous, organic phase into which the indicator is dissolved. The continuous phase is hydrophilic and absorbs water. The water in the continuous phase produces a significant change in pH, causing the dissolved indicator material to change in color. Such fatty acids are typically viscous liquid or solid materials comprising straight chain, saturated, and unsaturated fatty acids, dimer acids, rosin acids, hydrogenated rosin acids, tall oil, and others. Typically, carboxylic acids having an acid number greater than 100, and preferably greater than 140, are used in the hot-melt indicator materials of the invention.

ACID-BASE INDICATOR

Acid-base indicator is used in conjunction with the fatty acid material and the polyester material described above. Important characteristics of the acid-base, i.e., pH, indicator is that it be soluble in the hot-melt components and has a color change at a pH of about 2 to 5.6 and preferably, of about 3.8 to 5.4. This pH is one created by the interaction between moisture and the hot-melt components set forth above. Such a pH is created in the hot-melt indicator composition as moisture permeates the organic, hydrophilic material. Preferred acid-base indicators include Bromcresol Green, Bromphenol Blue, etc. Such indicators are present in an amount effective to produce a color change in the indicator composition such that the presence of moisture is detectable. Typically they are present in a concentration of about 0.03 to 0.5 wt-% of the hot-melt indicator composition.

The hot-melt indicator material of the invention is formulated using typical hot-melt blending techniques. The materials are typically blended in large manufacturing vessels with an inert atmosphere and agitation equipment. After blending the materials and the package in convenient sizes for sale, a preferred method of manufacturing involves first manufacturing a pre-blend of a small amount of fatty acid and indicator. Once the pre-blend is in place, the polyester material is added to a blending unit, melted and stirred until uniform. Into the melted polyester is added slowly the fatty acid material and any antioxidant used. Once uniform, the fatty acid/indicator pre-blend is added and the mixture is blended until smooth.

The above discussion provides a basis for understanding the invention. The following examples disclose preferred embodiments of the invention and contain a best mode.

EXAMPLE I

POLYESTER PREPARATION

Into an industrial heated blending apparatus equipped with agitation and a nitrogen blanket was added 40.91 parts of an ethylene-acrylic acid material having a melt viscosity of about 650 cP at 140° C. and containing about 23 percent by weight acrylic acid (Polyethylene AC 5180). When the ethylene-acrylic acid was fully melted at 210° F., 58.34 parts of a polyethylene oxide polymer, having a molecular weight of about 8,000 (CARBOWAX ®8000), was slowly added to the polymer melt such that the polyethylene oxide polymer was melted and incorporated into the melt rapidly. Once fully incorporated, 0.25 parts of a hindered phenol antioxidant (IRGANOX 1010) was added to the melt. The melt was blanketed with nitrogen and heated to approximately 300° F. Two tenths parts of a hydrated monobutyl tin (IV) oxide (FASCAT 4100) was added to the melt. The melt was placed under vacuum and the melt temperature was raised to 450° F. The melt was reacted for an extended period during which water of reaction was collected. The material was then cooled and an additional 0.25 parts of the antioxidant were added.

EXAMPLE II

HOT-MELT INDICATOR PREPARATION

Into a large heated agitator with a nitrogen atmosphere was placed about 67.9 parts by weight of the product of Example I. The material was melted and stirred until uniform.

Separately, approximately 0.4 parts by weight of a fatty acid material having an acid number of 160 (FORAL AX) was heated to 250° F. and blended with 0.1 parts by weight of Bromcresol Green. The pre-blend was agitated until the indicator material was fully wetted by the fatty acid.

Into the melted polyester was placed 29.6 parts by weight of a fatty acid material (FORAL AX) having an acid number of approximately 160, followed by 0.2 parts of a hindered phenol antioxidant (IRGANOX 1076). The materials were agitated at 250° F until smooth, and into the uniform melt was placed 0.5 parts of the fatty acids/indicator pre-mix. After addition, the melt was mixed until smooth and drawn off into storage.

EXAMPLE III

A sample of the product of Example I was aged at 275° F. in an oven. The material was examined after 16 hours and after 4 days at 275° F. In both instances, no phase separation had occurred, and the material appeared turbid. The results therefore indicate that the polyester, according to the present invention, is phase stable at hot-melt pot temperatures.

EXAMPLE IV

HOT-MELT INDICATOR STABILITY

A polyester was prepared according to the procedure of Example I from about 40.81 parts of an ethyleneacrylic acid material having a melt viscosity of 650 cP at 140° C. and containing 23 percent by weight acrylic acid and about 58.19 parts of a polyethylene oxide polymer having a molecular weight of about 8000 in the presence of about 0.5 parts of a hydrated monobutyl tin (IV) oxide. A hot-melt indicator was then prepared according to the process of Example II using about 69.7 parts of the above polyester, about 30 parts of the fatty acid material having an acid number of about 160, and about 0.1 parts of Bromcresol Green.

The hot-melt indicator was then placed in an oven at about 200° F. The material was then inspected periodically. The results are shown below in Table 1.

TABLE 1

High Temperature Stability of the Hot-Melt Indicator of Example IV

| Time at Observance (days) | Temperature (°F.) | Comments |
|---|---|---|
| 3 | 200 | Smooth, good looking, no separation, some grit on bottom |
| 4 | 210 | Smooth, good looking, no separation, some grit on bottom |
| 5 | 250 | Smooth, good looking, no separation, some grit on bottom |
| 7 | 250 | No separation; very little aged color change, if any; moisture indication not affected. |

EXAMPLE V

A polyester was prepared according to the procedure of Example I from about 27.64 parts of an ethyleneacrylic acid material having a melt viscosity of 650 cP at 140° C. and containing 23 percent by weight of acrylic acid and about 71.61 parts of a monomethoxy capped polyethylene oxide polymer having a molecular weight of about 5000 in the presence of about 0.25 parts of hydrated monobutyl tin (IV) oxide and 0.5 parts of a hindered phenol antioxidant. The above polyester was aged in a 275° F. oven. It did not phase separate after 4 days at 275° F.

COMPARATIVE EXAMPLE

A hot-melt indicator was then prepared from a melt blend of about 28.51 parts of an ethylene-acrylic acid material having a melt viscosity of 650 cP at 140° C. and containing 23 percent by weight acrylic acid and about 40.66 parts of a polyethylene oxide polymer having a molecular weight of about 8000, and about 0.35 parts of a hindered phenol antioxidant. About 30 parts of the fatty acid material having an acid number of about 160 and about 0.1 parts of Bromcresol Green were added to the above blend to form a hot-melt indicator. The hot-melt indicator was oven aged and began to separate into two phases after 2 hours. These results indicate that a simple hot-melt indicator blend (formulated from an unreacted blend of the above ethyleneacrylic acid and polyethylene oxide) is not phase stable when left unagitated at hot-melt pot temperatures.

From the specification, examples and data, it can be seen that the hot-melt indicator of our invention exhibits excellent phase stability and pot life while maintaining its moisture indication properties.

The above discussions, examples and data provide a basis for understanding the invention. However, many embodiments of the invention can be made without departing from the spirit and scope of the invention. The invention is defined by the claims hereinafter appended.

What is claimed is:

1. A disposable article for use as an infant diaper or adult incontinent pad comprising a film-backing sheet and an absorbent layer; wherein extruded to the film-backing sheet is a hot-melt moisture indicator composition which comprises:

(a) about 50 to 90 wt-% of a polyester reaction product between a copolymer of ethylene and an ethylenically unsaturated monomer having pendant carboxylic acid units, and a hydroxy compound of the formula $H(OCH_2CH_2)_nOH$, or $CH_3(OCH_2CH_2)_nOH$, wherein n is about 45 to 300;

(b) about 10 to 50 wt-% of a rosin acid compound having an acid number of at least about 140; and (c) about 0.03 to 0.5 wt-% of an acid-base indicator that can change color at a pH of about 2 to 5.6.

2. The composition of claim 1 wherein the copolymer comprises an ethylene-acrylic acid copolymer.

3. The composition of claim 2 wherein the copolymer contains about 15 to 30 wt-% acrylic acid.

4. The composition of claim 3 wherein the copolymer contains about 19 to 26 wt-% acrylic acid.

5. The composition of claim 4 wherein the hydroxy compound has a molecular weight of about 5,000 to 10,000.

6. The composition of claim 5 wherein the indicator comprises Bromcresol Green.

7. The composition of claim 6 wherein the copolymer has an acid number within the range of about 117 to 234.

* * * * *